US009588234B2

(12) United States Patent
Watson et al.

(10) Patent No.: US 9,588,234 B2
(45) Date of Patent: Mar. 7, 2017

(54) MINIATURE, MOBILE X-RAY COMPUTED RADIOGRAPHY SYSTEM

(71) Applicant: Los Alamos National Security, LLC, Los Alamos, NM (US)

(72) Inventors: Scott A Watson, Los Alamos, NM (US); Evan A Rose, Los Alamos, NM (US)

(*) Notice: Subject to any disclaimer, the term of this patent is extended or adjusted under 35 U.S.C. 154(b) by 361 days.

(21) Appl. No.: 14/258,481

(22) Filed: Apr. 22, 2014

(65) Prior Publication Data
US 2015/0078520 A1    Mar. 19, 2015

Related U.S. Application Data

(60) Provisional application No. 61/814,430, filed on Apr. 22, 2013.

(51) Int. Cl.
*G01T 1/20* (2006.01)
*G01N 23/04* (2006.01)

(52) U.S. Cl.
CPC ........... *G01T 1/2014* (2013.01); *G01N 23/04* (2013.01); *G01T 1/2012* (2013.01); *G01N 2223/301* (2013.01); *G01N 2223/308* (2013.01)

(58) Field of Classification Search
CPC ...... G01N 23/04; G01T 1/2012; G01T 1/2014
USPC ... 378/53, 62, 98.3; 250/581, 582, 583, 584, 250/585, 586
See application file for complete search history.

(56) References Cited

U.S. PATENT DOCUMENTS

| | | | |
|---|---|---|---|
| 4,258,264 A | 3/1981 | Kotera et al. | |
| 4,933,558 A | 6/1990 | Carter et al. | |
| 4,953,038 A | 8/1990 | Schiebel et al. | |
| 5,747,825 A | 5/1998 | Gilblom et al. | |
| 6,169,782 B1 * | 1/2001 | Zetterlund | H05G 1/12 378/101 |
| 6,259,112 B1 * | 7/2001 | Lim | G01N 23/223 250/271 |
| 6,392,248 B1 * | 5/2002 | Takahara | G21K 4/00 250/306 |
| 6,417,518 B2 * | 7/2002 | Arakawa | G01T 1/2014 250/587 |
| 6,707,058 B2 * | 3/2004 | Akimoto | G03B 42/08 250/585 |
| 6,759,673 B2 * | 7/2004 | Akimoto | G01T 1/2014 250/484.4 |
| 7,026,638 B2 * | 4/2006 | Kerr | G03B 42/08 250/585 |
| 7,071,483 B2 * | 7/2006 | Kerr | G03B 42/08 250/585 |

(Continued)

OTHER PUBLICATIONS

Paul Leblans, Dirk Vandenbroucke, and Peter Willems. Storage Phosphors for Medical Imaging. Materials 2011, 4, 1034-1086.*

(Continued)

*Primary Examiner* — Allen C. Ho
(74) *Attorney, Agent, or Firm* — LeonardPatel PC

(57) ABSTRACT

A miniature, portable x-ray system may be configured to scan images stored on a phosphor. A flash circuit may be configured to project red light onto a phosphor and receive blue light from the phosphor. A digital monochrome camera may be configured to receive the blue light to capture an article near the phosphor.

20 Claims, 5 Drawing Sheets

(56) References Cited

U.S. PATENT DOCUMENTS

| | | | | |
|---|---|---|---|---|
| 7,129,511 B2* | 10/2006 | Baek | ............... | G03B 42/08 250/586 |
| 7,176,465 B2* | 2/2007 | Kerr | ............... | G01T 1/2014 250/336.1 |
| 7,186,996 B2* | 3/2007 | Struye | ............... | G03B 42/08 250/581 |
| 7,227,167 B2* | 6/2007 | Leblans | ............... | G01T 1/2012 250/584 |
| 7,244,955 B2 | 7/2007 | Bueno et al. | | |
| 7,313,224 B1* | 12/2007 | Saunders | ............... | A61B 6/544 378/108 |
| 7,378,676 B2* | 5/2008 | Struye | ............... | C09K 11/7733 250/583 |
| 7,410,264 B2* | 8/2008 | Yamasaki | ............... | G02B 27/0911 348/801 |
| 7,504,648 B2* | 3/2009 | Boutet | ............... | G03B 42/08 250/237 G |
| 7,895,393 B2 | 2/2011 | Li | | |
| 7,982,202 B2* | 7/2011 | Boutet | ............... | G02B 7/1821 250/584 |
| 8,558,207 B2* | 10/2013 | Berger | ............... | G01T 1/2014 250/484.4 |

OTHER PUBLICATIONS

Heinz von Seggern. Photostimulable X-Ray Storage Phosphors: a Review of Present Understanding. Brazilian Journal of Physics, vol. 29, No. 2, Jun. 1999, 254-268.*

Scott A. Warren et al., "MiniMAX: miniature, mobile, agile, x-ray system," published in SPIE Proceedings, vol. 8371, on Apr. 23, 2012.

Scott Warren et al., "MiniMAX Miniature, Mobile, Agile, X-ray System" for 2013 R & D Joint Entry, approximate publication date Jun. 2013.

Scott Watson et al., A Compact, Portable X-Ray System for Field Inspection published at IAEA "International Conference on Nuclear Security" on Jul. 1-5, 2013.

\* cited by examiner

500

MINIATURE, MOBILE X-RAY COMPUTED RADIOGRAPHY SYSTEM

CROSS REFERENCE TO RELATED APPLICATION

This application claims priority to U.S. Provisional Patent Application Ser. No. 61/814,430 filed on Apr. 22, 2013. The subject matter of the earlier filed provisional application is hereby incorporated by reference in its entirety.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD

The present invention relates generally to the field of x-ray, and particle radiography and imaging, and more particularly, to the sensing, detection, and monitoring of an article using x-ray radiographic techniques.

BACKGROUND

Conventional computed radiography (CR) scanners use a red laser-flying spot to liberate blue, photo-stimulated, emission light. For example, FIG. 1 shows a conventional CR scanner 100. Conventional CR Scanner 100 includes a red laser flying spot 110 that emits red light to a moving reflector 115. Moving reflector 115 reflects and directs the red light to a phosphor 105 that emits blue light back to a receiver 120 such as a photomultiplier tube. In conventional CR scanners, a single section of an article lying on phosphor 105 is scanned at a time. To scan images relatively quickly, phosphor 105 must have a fast relaxation time.

However, this process is slow and requires complex transport mechanisms, sophisticated readout electronics, and a large scanner. Thus, a smaller and faster x-ray system, with fewer moving parts, may be beneficial.

SUMMARY

Certain embodiments of the present invention may provide solutions to the problems and needs in the art that have not yet been fully identified, appreciated, or solved by scanning and/or imaging devices. For example, an x-ray system may be configured to scan images stored on a storage phosphor in some embodiments. Both the storage phosphors and the scanned images may be tiled into a larger, image mosaic. The system may be handheld, lightweight, and readily deployable around the world in any number of applications in many embodiments.

In one embodiment, an apparatus includes a flash circuit configured to project a short flash of red light onto a phosphor, and receive blue light from the phosphor. The apparatus also includes a digital monochrome camera configured to receive the blue light to capture an image of an article near the phosphor.

In another embodiment, a system includes a monochrome camera configured to scan one or more images of an article recorded on one or more phosphors such that the one or more images can form a complete mosaic of the article. The system also includes a plurality of lights configured to project focused red light onto a phosphor, and a filter configured to reject the red light projected onto the phosphor, and pass blue light from the phosphor to the monochrome camera.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Embodiments of the present invention pertain to a miniature, mobile x-ray system for sensing, detecting, and monitoring of an article or ionizing radiation signature, and, more particularly, to detecting any ionizing radiation including hard ultra violet (UV), beta, alpha, neutron, x-ray, gamma-ray, and proton radiography. The system may be a small, lightweight digital x-ray system that scans images recorded on a storage phosphor screen. The system may include a camera, lights, and a filter, and a storage phosphor. These components may allow the system to seamlessly perform x-ray to electro-optic conversion. Scanned images can then be tiled into large image mosaics in some embodiments. This process results in a high resolution x-ray image of virtually unlimited size and of any x-ray energy in some embodiments, all from a single exposure.

Figure 2:
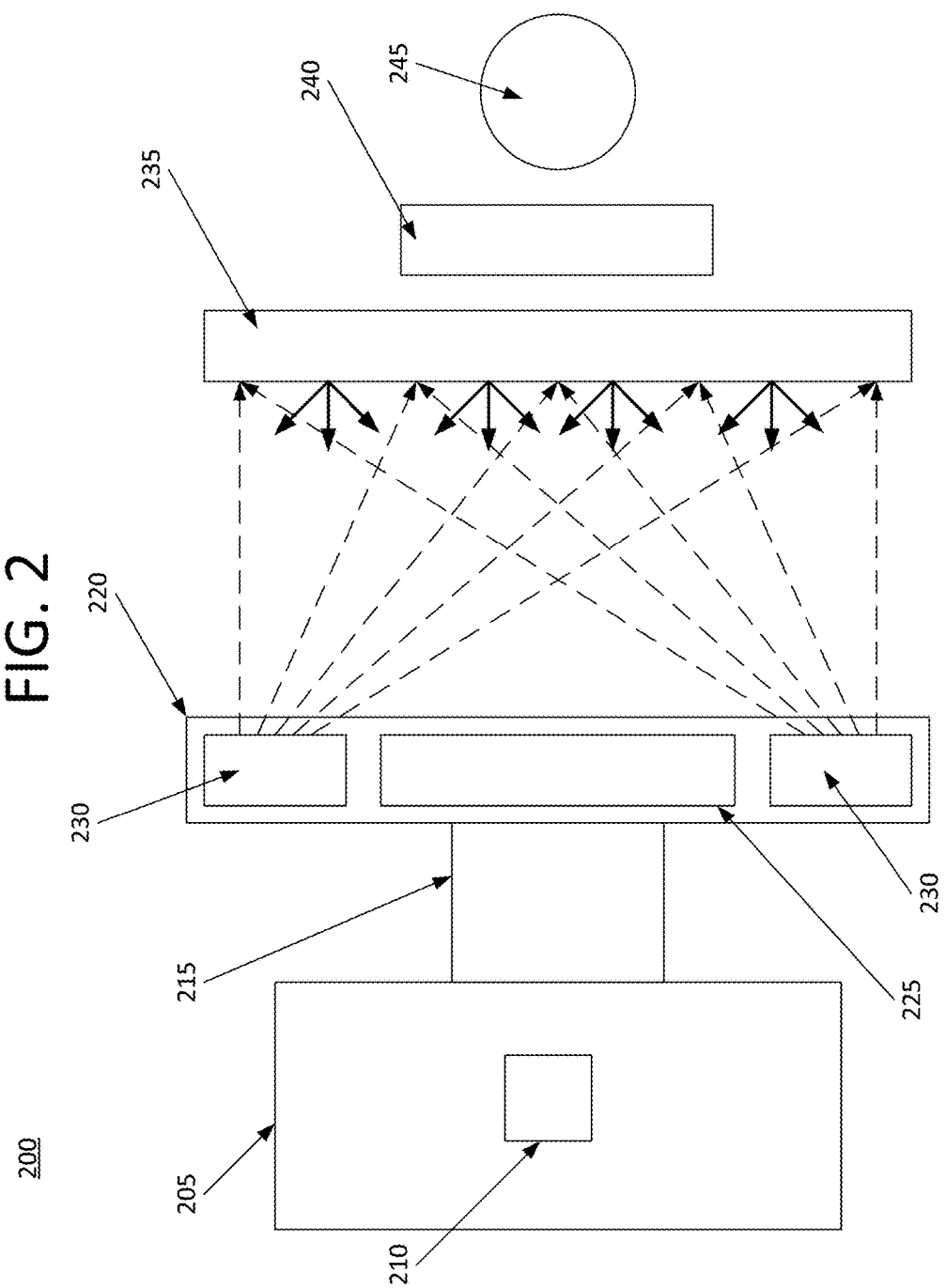
FIG. 2 is a block diagram illustrating an x-ray system, according to an embodiment of the present invention.

FIG. 2 is a block diagram illustrating an x-ray system 200, according to an embodiment of the present invention. X-ray system 200 includes a lightweight x-ray source 245. Lightweight x-ray source 245 is configured to irradiate an article 240 with photons in the x-ray region of the electromagnetic spectrum, or with other ionizing particles, such that a transmission image of article 240 can be generated. In some embodiments, lightweight x-ray source 245 may be a $^{57}Co$ gamma ray source, $^{137}Cs$, $^{60}Co$, $^{192}Ir$, $^{75}Se$, $^{99}Tc$, or any radioisotope. This reduces the weight and size of lightweight x-ray source 245 as compared to conventional systems.

In certain embodiments, lightweight x-ray source 245 may be a triboluminescent source. Also, in some embodiments, lightweight x-ray source 245 may include a sealed cold cathode x-ray tube, as described in U.S. patent application Ser. No. 14/181,278, filed on Feb. 14, 2014. The sealed cold cathode x-ray tube may be a pierce-type x-ray tube source that allows lightweight x-ray source 245 to operate at higher energy levels.

X-ray system 200 also includes a camera 205. To improve the quality of the scanned image, camera 205 may be a digital monochrome camera. The digital monochrome camera may be a charged-couple device (CCD) camera, a complementary metal oxide silicon (CMOS) camera, a charge injection device (CID) camera, an amorphous silicon panel, or any digital monochrome camera that would be appreciated by a person of ordinary skill in the art.

Attached to camera 205 is a lens 215. Lens 215 may be a fast lens in some embodiments having high resolution with very low "ghosting" and vignetting. Lens 215 is a fixed conjugate lens or a fixed format lens in this embodiment. This allows the image to sit in a single place without having a focus ring on the image. Lens 215 is also lightweight reducing the overall weight of x-ray system 200.

Attached to lens 215 is a light box 220. Light box 220 includes a filter 225 and a plurality of lights 230. Filter 225 may be part of light box 220, or may be a separate unit that can be affixed to light box 220. Filter 225 may be a blue pass filter (e.g., a two-sided coded filter) configured to pass blue light and reject red light. As shown in FIG. 2, red light (the dashed lines) is projected onto phosphor 235 using plurality of lights 230. Blue light (the solid lines) is emitted back from phosphor 235 and passes through filter 225. While this embodiment includes a single filter, multiple filters can be used in other embodiments. For example, multiple filters may be used to further eliminate infrared light, stray light, or other light that would reduce the quality of the scanned image. A more detailed description of light box 220 is discussed below with respect to FIG. 3.

Figure 3:
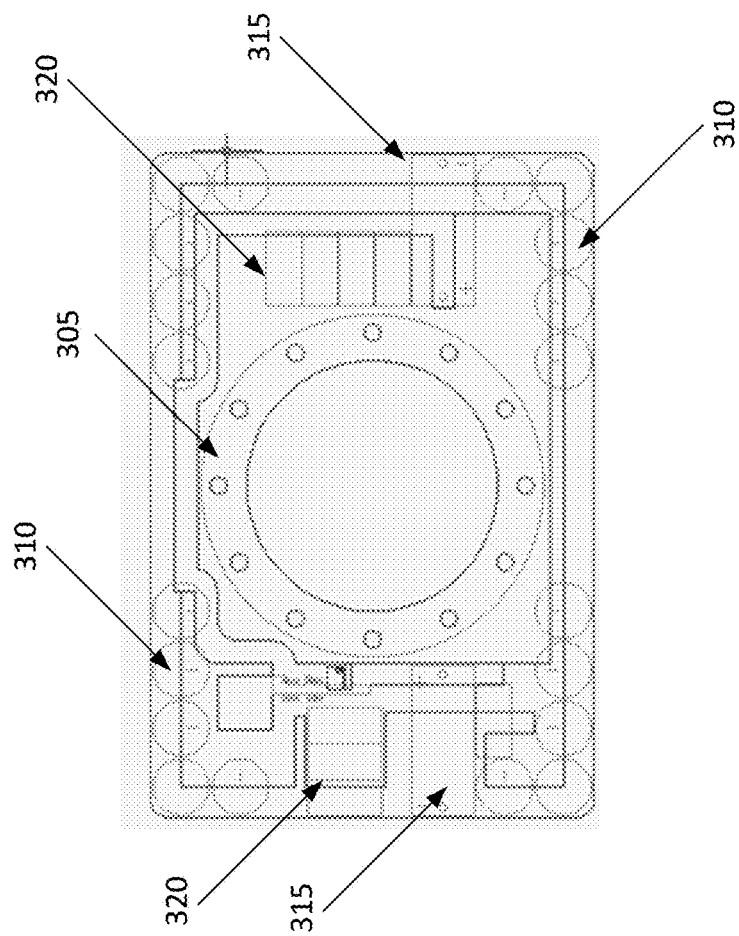
FIG. 3 is a circuit diagram illustrating a flash circuit, according to an embodiment of the present invention.

FIG. 3 is a circuit diagram illustrating a flash circuit 300 of light box 220 of FIG. 2, according to an embodiment of the present invention. In this embodiment, flash circuit 300 includes a filter 305 and a plurality of lights 310. In other embodiments, filter 305 may be separate from flash circuit 300. Filter 305 in this embodiment is a very high rejection, "short-pass", dichroic filter configured to permit substantial transmission of photons in a predefined wavelength range while substantially rejecting photons in the long wavelength range, e.g., in a range that is greater than 500 nm.

Also, in this embodiment, plurality of lights 310 surround filter 305, and the number of plurality of lights 310 used depends on the configuration of flash circuit 300 and the image quality desired. Plurality of lights 310 are situated such that the article being scanned on phosphor 235 is over-illuminated with red light to allow the blue light to be collected. This prevents under-illumination of a particular area of the article and reduces the effect of pattern light.

In this embodiment, plurality of lights 310 may be light emitting diodes (LEDs). Because LEDs project light in a broad manner, each LED includes a condenser lens (not shown). The condenser lens is configured to focus light from the LEDs to phosphor 235, or redirect the light in a forward direction such that the light can be used in a more effective manner. By attaching a condenser lens to each LED, the number of LEDs required to project the light can also be reduced. This allows for an overall reduction in weight and size of the flash circuit, increase in facilitation of hand-held operation, or operation in well-lit ambient conditions.

In other embodiments, plurality of lights 310 may be laser diodes with diffractive optics. Laser diodes provide various benefits over other types of lights. For example, laser diodes can project a coherent pattern suitable for multiple image formats. Also, the illumination source from the laser diodes is generally smaller. Further, the weight and size of plurality of lights 310 can be reduced. This reduction in weight and size allows the overall size of flash circuit 300 to also be reduced. Because the weight and size of flash circuit 300 is reduced, the entire system can be even more compact, while maintaining or improving the quality of the scanned image.

It should also be appreciated that while LEDs spread light over a wide solid angle, laser diodes are more coherent. For instance, light from laser diodes can be projected to be identical to the size of phosphor 235, while light from the LEDs is generally projected not only on phosphor 235, but also to areas outside of phosphor 235. In other words, the light emitted from the laser diodes is more effectively used than light emitted from the LEDs.

Flash circuit 300 also includes batteries 315 and capacitors 320 to form a pulse power unit. While FIG. 3 shows two batteries 315, any number of batteries may be used. Also, the number of capacitors 320 may vary in order to achieve a high energy storage. In should be appreciated that each "super" capacitor 320 has a high capacity of around 5-10 farads in this embodiment. Capacitors 320 may also be called supercapacitors in this embodiment.

The pulse power unit is configured to use high density energy from capacitors 320 to power plurality of lights 310. The pulse power unit is configured to switch the high current from energy-dense capacitors 320 on plurality of lights 310. This may require high-current, low impedance circuitry e.g. Trench Field Effect Transistor (FET) switches and heavy gauge copper. In essence, capacitors 320 compensate for the reduction in the number of batteries 315. This allows flash circuit 300 to be lighter as less batteries 315 are required to operate flash circuit 300.

Because flash circuit 300 supplies high levels of current, a low impedance-load may be needed. To achieve a low impedance-load, flash circuit 300 may include heavy gauge copper. However, it should be appreciated that any substrate having low impedance may be used.

Returning to FIG. 2, affixed to camera 205 is a hot shoe 210. Hot shoe 210 is configured to develop phosphor 235 in a flash mode. Hot shoe 210 may include a push-button (not shown) configured to erase, or clear, phosphor 235 for subsequent use. This adaptation eliminates the need for a separate illumination device that is normally as large as or the same size as phosphor 235.

Figure 1:
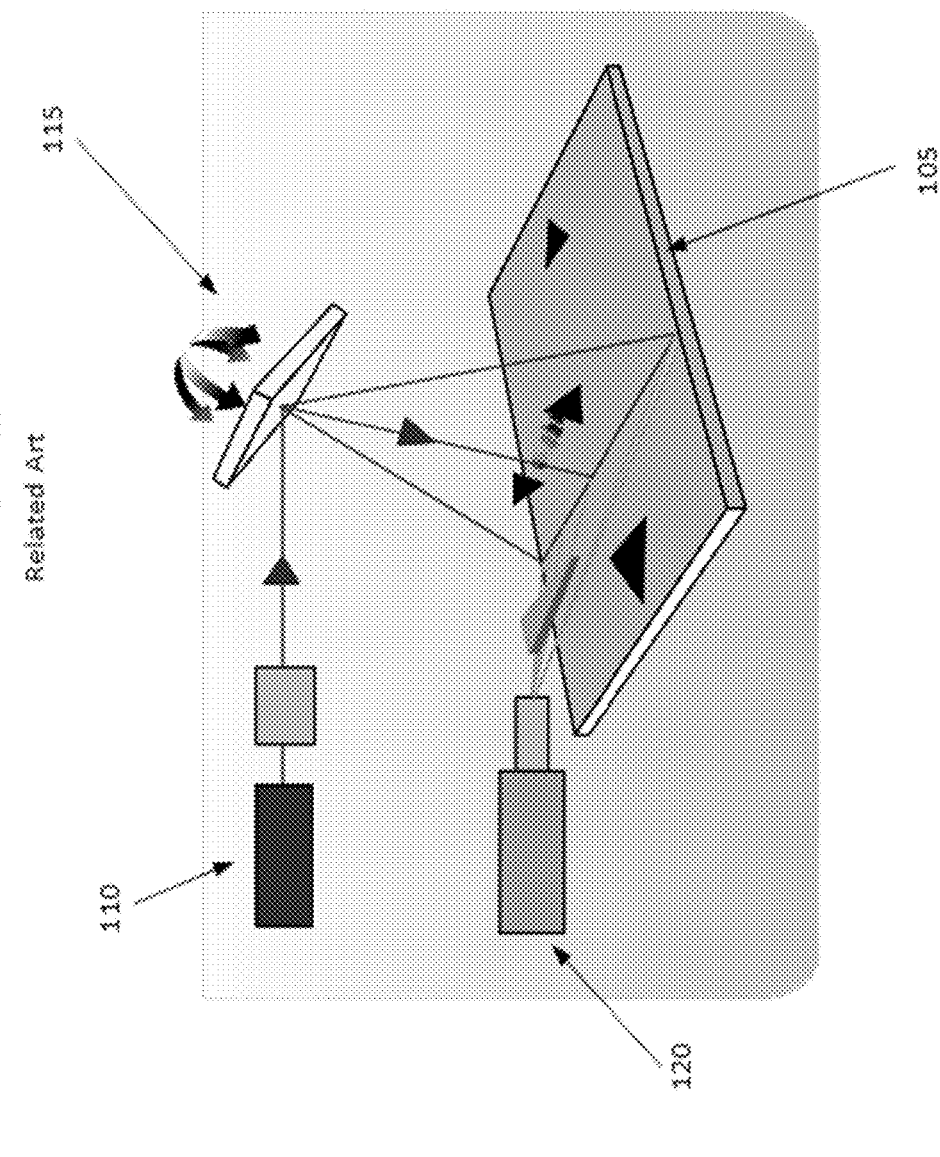
FIG. 1 illustrates a conventional CR scanner.

As discussed earlier, a conventional CR scanner 100, as shown in FIG. 1, has a blur as large as the width of a laser causing a smearing of the image to occur. However, by using a phosphor 235, as shown in FIG. 2, smearing is eliminated, substantially increasing resolution of the scanned article. In this embodiment, phosphor 325 allows an article to be scanned at a quicker rate than conventional CR scanners because the entire image of the scanned article is taken at a single time.

It should be appreciated that phosphor 235 in this embodiment is different from conventional phosphors. As noted above, conventional phosphors have fast relaxation, allowing conventional CR scanner 100 to scan an article in segments. However, in this embodiment, phosphor 235 may have a fast (less than 1 microsecond) or slow relaxation of up to many seconds since the red light from plurality of lights 230 illuminates all of phosphor 235 at the same time. This feature enables x-ray system 200 to have far greater utility due to the very large numbers of available and potentially produced storage phosphor molecules, which have "slow" relaxation. These molecules, which have been heretofore rejected due to their slow relaxation time, can now be advantageously used based upon other physical properties (e.g., density).

Because x-ray system 200 uses a portable camera 205, phosphor 235 can be placed on any surface, e.g., planar surface or non-planar surface, to create a radiation detector of arbitrary size and shape. For example, phosphor 235 can be painted on a surface of a wall, inside of a transportation container, or on any suitable article or object, while allowing for an article to be scanned. Stated another way, by painting phosphor 235 on a surface, the surface can be turned into an imager.

It should be appreciated that phosphor 235 has different readout mechanics than conventional phosphors. For example, in a conventional phosphor scanner, a phosphor plate must run through the scanner. In x-ray system 200, phosphor 235 may remain in place or stationary at all times during operation while the camera 205 is moved to phosphor 235, greatly increasing the overall utility of x-ray system 200.

Figure 4:
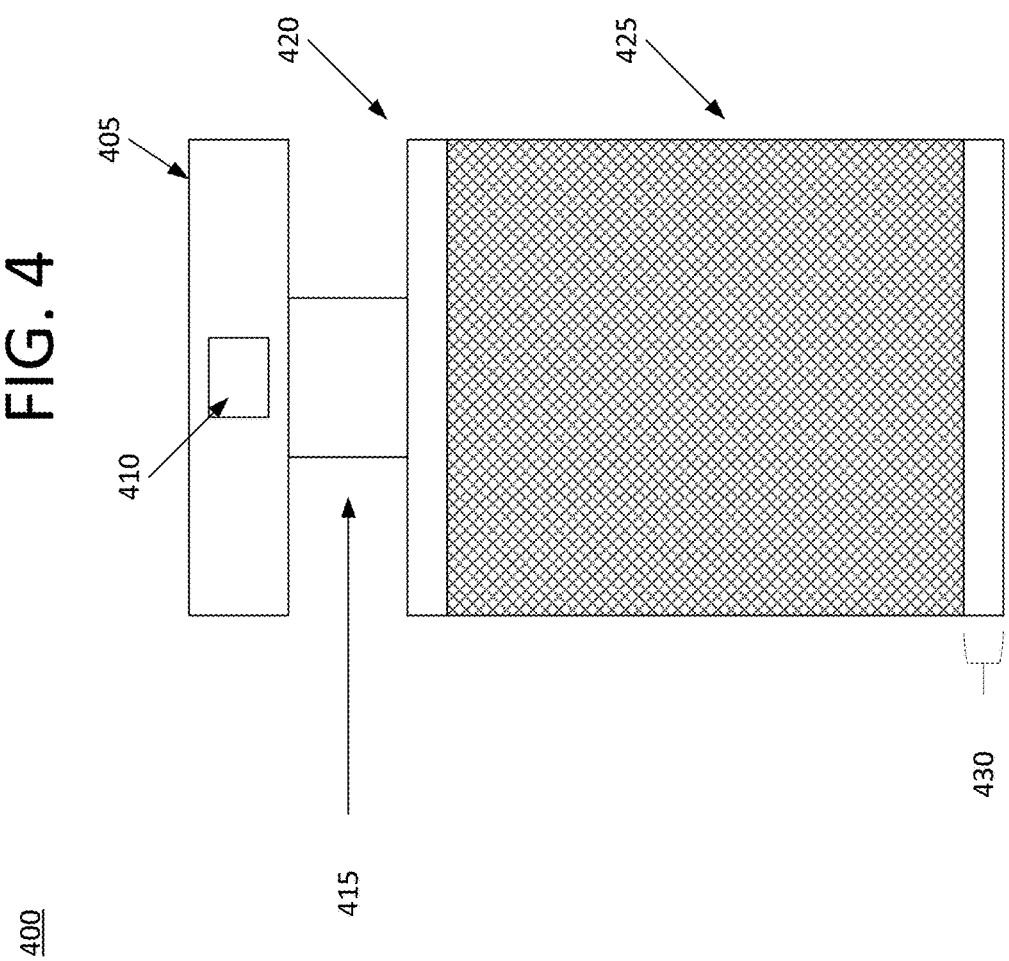
FIG. 4 is a block diagram illustrating an x-ray system, according to an embodiment of the present invention.

FIG. 4 is a block diagram illustrating x-ray system 400, according to an embodiment of the present invention. In this embodiment, x-ray system 400 includes a box 425 composed of carbon fiber material. Box 425 can be unfolded into a flat panel or remain in a folded state to carry camera 405, hot shoe 410, lens 415, light and filter device 420, and phosphor 430.

In certain embodiments, box 425 may also act as a portable dark room, preventing ambient light from entering and either erasing phosphor 430, or producing unwanted image signal. As illustrated in FIG. 4, box 425 may be placed on top of, or around, phosphor 430. The article to be scanned can be placed underneath phosphor 430. Camera 405, lens 415, and light and filter device 420 can be placed on top of box 425 to create the portable dark room. This allows an image to remain focused.

Box 425 may also include a connecting unit (not shown) allowing camera 405, lens 415, and light and filter device 420 to be attached to box 425. The connecting unit may include Velcro®, latches, etc. The connecting unit may help maintain stability of x-ray system 400 when scanning an article.

Box 425 may also include thin walls. This is beneficial when taking multiple images of a larger object. For example, the thin walls allow for little separation between scanned images so a complete mosaic can be taken.

Figure 5:
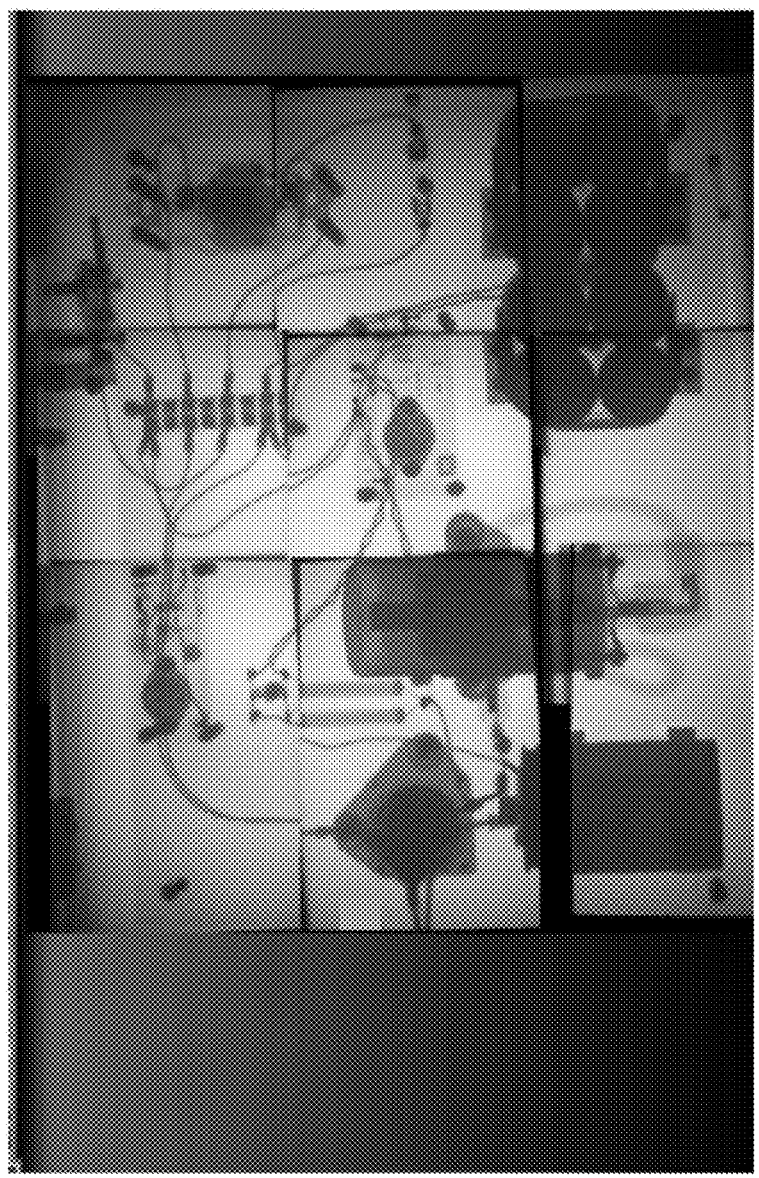
FIG. 5 shows an image produced by an x-ray system through a mosaic of multiple scans from a single radiograph, according to an embodiment of the present invention

When scanning larger articles such as a suitcase, conventional Direct Radiography (DR) systems utilize multiple high cost DR panels. The system of some embodiments, however, is configured to perform multiple scans on a large radiograph using only a camera and multiple, low cost storage phosphor panels. For example, FIG. 5 shows an image 500 produced by such a system through a mosaic of multiple scans from a single radiograph. Essentially, the system allows a large radiograph to be created with a small sensor and a single exposure.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A system, comprising:
   a flash circuit configured to project a short flash of red light directly onto a phosphor, and directly receive blue light from the phosphor; and
   a digital monochrome camera configured to receive the blue light to capture an image of an article near the phosphor; and
   a lens in between, and attached to, the flash circuit and the digital monochrome camera.

2. The system of claim 1, wherein
   the lens configured to allow the image to be situated in a single location without having a focus ring on or around the image.

3. The system of claim 1, wherein the flash circuit comprises a plurality of light emitting diodes configured to project the red light onto the phosphor.

4. The system of claim 3, further comprising:
   a condenser lens attached to each of the plurality of light emitting diode, the condenser lens configured to project focused red light onto the phosphor.

5. The system of claim 1, wherein the flash circuit further comprises a plurality of laser diodes configured to project focused red light onto the phosphor.

6. The system of claim 1, further comprises:
   at least one filter configured to reject the red light projected onto the phosphor and allow the blue light from the phosphor to pass through to the digital monochrome camera.

7. The system of claim 1, wherein the flash circuit comprises a pulse power unit,
   the pulse power unit comprises at least one battery and a plurality of capacitors.

8. The system of claim 7, wherein the flash circuit comprises a plurality of lights, and wherein the pulse power unit is configured to use high density energy from the plurality of capacitors to power the plurality of lights.

9. The system of claim 1, further comprising:
a hot shoe configured to develop the phosphor in a flash mode and erase the phosphor for subsequent use.

10. The system of claim 1, wherein the phosphor is painted or deposited on a planar or non-planar surface to create a radiation detector of arbitrary size and shape.

11. The system of claim 1, wherein the phosphor comprises slow relaxation storage-phosphor compounds.

12. The system of claim 1, wherein the phosphor is configured to remain stationary during operation.

13. The system of claim 1, further comprising:
a lightweight x-ray source configured to irradiate the article with photons ionizing particles such that a transmission image of the article can be generated.

14. The system of claim 1, further comprising:
a box configured to unfold into a flat panel or remain in a folded state, the box comprises the monochrome digital camera, the flash circuit, a hot shoe, a lens, and the phosphor.

15. The system of claim 14, wherein the box is further configured to create a portable dark room that prevents ambient light from entering the box.

16. The system of claim 14, wherein the box comprises walls configured to create minimum separation between scanned images so a complete mosaic of an article is taken.

17. A system, comprising:
a monochrome camera configured to directly scan one or more images of an article recorded on one or more phosphors such that the one or more images can form a complete mosaic of the article;
a flash circuit comprising:
  a plurality of lights configured to directly project focused red light onto the one or more phosphors; and
  a filter configured to reject the red light projected directly onto the one or more phosphors, and pass blue light received directly from the one or more phosphors to the monochrome camera; and
a lens in between, and attached to, the monochrome camera and the flash circuit.

18. The system of claim 17, further comprising:
a box is further configured to create a portable dark room to prevent ambient light from entering the box.

19. The system of claim 17, wherein the one or more phosphors are painted or deposited on a planar or non-planar surface to create a radiation detector of arbitrary size and shape.

20. The system of claim 17, further comprising:
a lightweight x-ray source configured to irradiate the article with photons ionizing particles such that a transmission image of the article can be generated.

* * * * *